United States Patent [19]

O'Connor et al.

[11] Patent Number: 4,533,485
[45] Date of Patent: Aug. 6, 1985

[54] ANIONIC SURFACTANT ADDITION PRODUCTS OF MALEIC OR FUMARIC ACID AND A POLY(OXYALKYLATED) ALCOHOL

[75] Inventors: James M. O'Connor, Clinton; Michael Scardera, Hamden; Frank R. Grosser, Bethany, all of Conn.

[73] Assignee: Olin Corporation, Cheshire, Conn.

[21] Appl. No.: 505,663

[22] Filed: Jun. 20, 1983

[51] Int. Cl.$^3$ .................. C11D 7/06; C07C 59/305; C07C 59/58; C07C 69/60

[52] U.S. Cl. ................... 252/156; 252/174.19; 252/174.21; 252/174.22; 252/546; 560/198; 562/583

[58] Field of Search ........... 560/198; 252/156, 174.21, 252/174.22, 546, 174.19; 562/583

[56] References Cited

U.S. PATENT DOCUMENTS

| | | | |
|---|---|---|---|
| 3,419,510 | 12/1968 | Hudak | 260/18 |
| 3,983,058 | 9/1976 | Hirooka et al. | 260/29 |
| 4,124,552 | 11/1978 | Koleske et al. | 260/29 |
| 4,207,227 | 6/1980 | von Bonin | 260/40 |
| 4,207,421 | 6/1980 | Scardera et al. | 568/625 |
| 4,250,077 | 2/1981 | von Bonin et al. | 260/37 |
| 4,263,413 | 4/1981 | Gardner et al. | 525/34 |
| 4,317,940 | 3/1982 | Scardera et al. | 568/625 |
| 4,365,024 | 12/1982 | Frentzel | 521/114 |

OTHER PUBLICATIONS

V. Malatesta and J. C. Scaiano, "Absolute Rate Constants for the Reactions of tert-Butoxyl with Ethers: Importance of the Stereoelectronic Effect", J. Org. Chem., 1982, 47, pp. 1455-1459.

*Primary Examiner*—Natalie Trousof
*Assistant Examiner*—Vera C. Clarke
*Attorney, Agent, or Firm*—William A. Simons; Thomas P. O'Day

[57] ABSTRACT

Described are anionic surfactants which are made by (1) reacting maleic acid or fumaric acid, or mixtures thereof with at least one selected poly(oxyalkylated) alcohol in the presence of a peroxy-type free radical initiator to form a carboxylic acid group-containing addition product and (2) neutralizing said addition product with a sufficient amount of a neutralizing agent to convert at least a major proportion of said carboxylic acid groups to salt groups. These surfactants exhibit excellent surface activity as well as being highly soluble in caustic solutions.

9 Claims, No Drawings

ANIONIC SURFACTANT ADDITION PRODUCTS OF MALEIC OR FUMARIC ACID AND A POLY(OXYALKYLATED) ALCOHOL

RELATED APPLICATIONS

This U.S. patent application is related to U.S. patent application Ser. No. 475,785 filed by Richard Frentzel on Mar. 16, 1983 and to U.S. patent application Ser. No. 475,786, filed by Richard Frentzel, Louis Rua, Jr. and Anne Pacheco on Mar. 16, 1983.

BACKGROUND OF THE INVENTION

1. Field Of The Invention

The present invention relates to the neutralized addition products of selected unsaturated dicarboxylic acids and selected poly(oxyalkylated) alcohols and their use as anionic surfactants suitable for use in caustic solutions.

2. Brief Description Of The Prior Art

Caustic-soluble surfactants are used today in a wide variety of industries. They are employed in the metal cleaning business to remove greases and process fluids from metal finishes. They are also used in the textile field to remove knitting oils and the like from textiles. They are used in emulsion polymerization reactions to aid the dispersion of one or more of the reactants in each other or in a solvent. They are also employed in dairy/food plants and in bottle washing operations, as well as household and other consumer cleaners.

Commonly used caustic-soluble surfactants include anionic alkylated diphenyl oxide disulfonate-type surfactants (e.g. DOWFAX 2A1 made by Dow Chemical Co. of Midland, Mich.); nonionic alkylated glucoside-type surfactants (e.g. TRITON BG-10 made by Rohm & Haas of Philadelphia, Pa.); and carboxylic acid-type surfactants (e.g. TRITON DF-20 also made by Rohm & Haas). While these commercially available surfactants may be suitable for certain applications, they have certain deficiencies which prevent their use in many applications. Ideally, an excellent caustic-soluble surfactant should have very good surface activity and high caustic solubility (e.g. soluble in aqueous solutions containing more than about 10% by weight NaOH) as well as low foaming properties and a relatively low cost.

Separately, reactions of carboxylic acids with polyols in the presence of a free radical initiator are known. For instance, U.S. Pat. No. 4,250,077 (von Bonin et al.) teaches mixing olefinically unsaturated carboxylic acids with many types of polyols and then polymerizing the mixture with a free radical former to produce a graft polymer. The preferred carboxylic acid (and the only acid used in the working examples) is acrylic acid, which homopolymerizes with itself. It should be noted that this reference does not teach the exact mechanism by which this "polymerization38 reaction is carried out.

U.S. Pat. No. 4,365,024 (Frentzel) teaches making surfactants suitable for incorporation in polyurethane foams by reacting under free radical polymerization conditions a polyoxyalkylene adduct and unsaturated dibasic esters containing 4 or 5 carbon atoms. The mechanism of this reaction is referred to as grafting, i.e. the reaction product is composed of the polyoxyalkylene adduct backbone to which are attached at intervals "grafts" of the unsaturated diester. See column 4, lines 46–51 of this patent. The patent further states that, "In light of the known inability of unsaturated diesters of the invention to homopolymerize, it is believed that the mechanism of the reaction may involve the addition of single diester units to the polyoxyalkylene backbone". The patent specifically teaches that these surfactants may be used in phenolic resin foams, polyisocyanurate foams and polyurethane foams.

U.S. patent application Ser. Nos. 475,785 (Frentzel) and 475,786 (Frentzel et al.), both filed on Mar. 16, 1983, teach making carboxylic acid-containing mono- and polyether polyol addition products by reacting maleic acid, fumaric acid, itaconic acid, or mixtures thereof with at least one polyhydroxy-containing mono- or polyether compound (e.g. a polyether diol or triol) in the presence of a peroxy free radical initiator. These patent applications also disclose making polyurethane prepolymers and aqueous polyurethane dispersions from these carboxylic acid-containing mono- and polyether polyol addition products.

Until the present invention, no one has proposed making surfactants by the free-radical addition of single carboxylic acid units at intervals onto the backbone of a poly(oxyalkylated) alcohol followed by neutralization of these carboxylic acid groups. It was quite surprising that these carboxylic acid-containing poly(oxyalkylated) alcohols have particularly useful properties as caustic-soluble surfactants. The individual single neutralized acid sites on the backbone provide adequate sites for providing caustic solubility, yet are short enough so as not to interfere with the surface activity and low-foaming properties of surfactant compositions as a whole.

BRIEF SUMMARY OF THE INVENTION

The present invention is, therefore, directed to an anionic surfactant composition made by the process comprising:

a. forming a carboxylic acid group-containing addition product by reacting in the presence of a peroxy-type free radical initiator an ethylenically unsaturated dicarboxylic acid selected from the group consisting of maleic acid, fumaric acid, and mixtures thereof with at least one poly(oxyalkylated) alcohol having the formula (I):

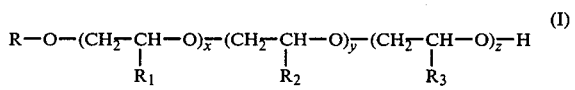

$$R-O-(CH_2-CH-O)_{\overline{x}}(CH_2-CH-O)_{\overline{y}}-(CH_2-CH-O)_{\overline{z}}-H \quad (I)$$
$$\phantom{R-O-(CH_2-CH-O)_x}|\phantom{(CH_2-CH-O)_y}|\phantom{(CH_2-CH-O)_z}|$$
$$\phantom{R-O-(CH_2-CH-O)_x}R_1 \phantom{(CH_2-CH-O)_y}R_2 \phantom{(CH_2-CH-O)_z}R_3$$

wherein R is a hydrocarbon-containing radical having an average of from about 6 to about 18 carbon atoms; $R_1$, $R_2$ and $R_3$ are individually selected from hydrogen and methyl with the proviso that $R_2$ is different than $R_1$ and $R_3$; x is an integer having a value from 1 to about 25; y is an integer having a value from 1 to about 25; z is an integer from about 0 to about 25; and the weight ratio of the poly(oxyalkylated) alcohol reactant to the dicarboxylic acid reactant being from about 95:5 to about 40:60; and b. neutralizing the formed addition product with a sufficient amount of a neutralizing agent to convert at least a major portion of the carboxylic acid groups in said addition product to salt groups.

The present invention is also directed to use of these surfactant compositions as surfactants and emulsifiers in aqueous systems, particularly aqueous systems containing more than about 10% by weight of an alkali metal hydroxide (e.g. NaOH).

DETAILED DESCRIPTION

1. Preparation Of Carboxylic Acid Group-Containing Addition Product

While the present invention is not to be so limited, this free radical initiated addition reaction is believed to occur by a three-step mechanism, which is illustrated by the following Equations (I) through (X) wherein the poly(oxyalkylated) alcohol employed is represented by A; one of the selected acids is represented by B; and the peroxy-type free radical initiator is presented by ROOR:

Initiation:

$$ROOR \rightarrow 2RO \cdot \quad (I)$$

Propagation:

$$A + RO \cdot \rightarrow A \cdot + ROH \quad (II)$$

$$A \cdot + B \rightarrow A\text{-}B \cdot \quad (III)$$

$$A\text{-}B \cdot + A \rightarrow A\text{-}B + A \cdot \quad (IV)$$

$$A\text{-}B \cdot + ROOR \rightarrow A\text{-}B\text{-}OR + RO \cdot \quad (V)$$

$$A\text{-}B \cdot + ROH \rightarrow A\text{-}B + RO \cdot \quad (VI)$$

Termination:

$$2RO \cdot \rightarrow ROOR \quad (VII)$$

$$A \cdot + A \cdot \rightarrow A\text{-}A \quad (VIII)$$

$$AB \cdot + A \cdot \rightarrow A\text{-}B\text{-}A \quad (IX)$$

$$AB \cdot + AB \cdot \rightarrow ABBA \quad (X)$$

In the case where the poly(oxyalkylated) alcohol (A) is $C_6H_{14}O.3$ moles oxypropyl.8 moles oxyethyl and the acid (B) is either maleic acid [cis—HOOCCH=CH-COOH] or fumaric acid (trans—HOOCCH=CH-COOH], Equations (II), (III) and (IV) would be written respectively as Equations (IIa), (IIIa) and (IVa) as shown below:

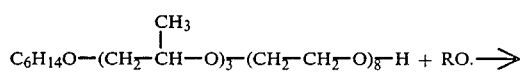

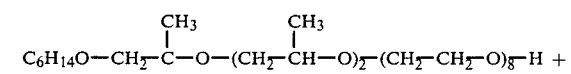

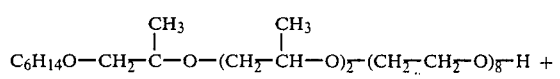

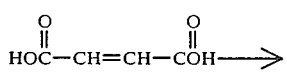

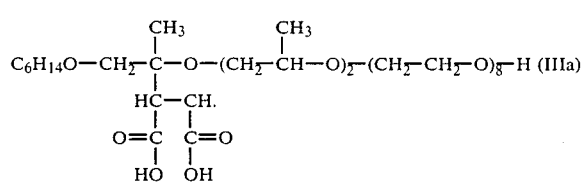

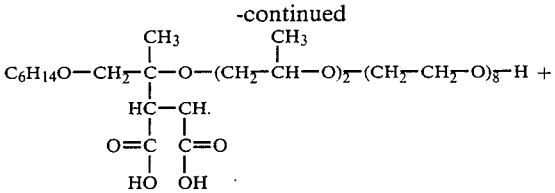

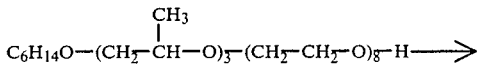

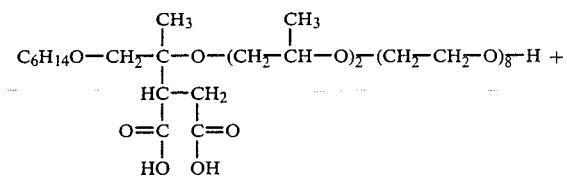

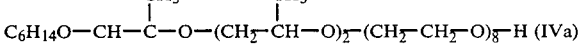

As can be seen in Equation (IIIa), above, the carboxylic acid replaces a hydrogen atom on a carbon adjacent to an oxygen atom in an ether linkage (C—O—C). With $C_6H_{14}.3PO.8EO$ as the poly(oxyalkylated) alcohol, there are a total of 23 sites where it is believed the acid groups may replace a hydrogen. These sites are the carbon atoms adjacent to an ether-oxygen. Thus, it is possible in theory that individual carboxylic acid groups may attach to all twenty-three sites on this particular poly(oxyalkylated) alcohol. In practice, it is believed that steric effects will prevent the attachment of that many acid groups as close to each other on the alcohol.

Maleic acid, fumaric acid and are the only known ethylenically unsaturated dicarboxylic acids that are suitable for this invention because they do not homopolymerize. Free radical addition reactions with them are completed by removal of a hydrogen from another polyol [see Equation (IV) above] or from another hydrogen atom source. Furthermore, it has been found that these carboxylic acids [when reacted to poly(oxyalkylated) alcohols according to the present invention] are particularly suitable for making caustic-soluble surfactants.

Suitable poly(oxyalkylated) alcohols for the present invention include the following types:

$$RO\text{—}(PO)_x\text{—}(EO)_y\text{—}H$$

$$RO\text{—}(EO)_x\text{—}(PO)_y\text{—}H$$

$$RO\text{—}(PO)_x\text{—}(EO)_y\text{—}(PO)_z\text{—}H$$

$$RO\text{—}(EO)_x\text{—}(PO)_y\text{—}(EO)_z\text{—}H$$

wherein R, x, y, and z are as defined above and PO and EO stand for propylene oxide and ethylene oxide groups, respectively. Preferably, R is a linear, aliphatic hydrocarbon radical having an average of from about 8 to about 16 carbon atoms. It is believed that alkylphenols such as octylphenol, nonylphenol, and higher alkylphenols may be also employed in this invention. Preferably, x is an integer having a value from about 2 to about 12. Preferably, y is an integer having a value from about 2 to about 15. And preferably, z is an integer having a value from about 0 to about 15. The ether linkages in these poly(oxyalkylated) alcohols are needed to form the formation of free radicals on the adjacent carbons. See V. Malatesta and J. C. Scaiano, "Absolute Rate Constants for the Reaction of tert-Butoxyl with Ethers: Importance of Stereoelectronic Effect", *J. Org. Chem.* 1982, 47 pages 1455–1459.

Poly(oxyalkylated) alcohols of the class RO—$(EO)_x$—$(PO)_y$—H may be made by methods similar to those described in U.S. Pat. No. 4,207,421, which issued to M. Scardera and F. Grosser on June 10, 1980. The disclosure of this patent is incorporated herein by reference in its entirety. Generally poly(oxyalkylated) alcohols of this class may be made by condensing an aliphatic alcohol, or mixture of alcohols, of desired average chain length with ethylene oxide followed by capping this condensation product with propylene oxide. The moles of ethylene oxide (EO) and propylene oxide (PO) employed per mole of alcohol will fall within the ranges for x and y as given above. The methods used for condensing and capping may be any of the well-known methods described in the art. Preferably, these reactions occur at elevated temperatures in the range of about 140° C. to about 200° C. (more preferably from about 160° C.–180° C.) It is also preferred to carry out such reactions in the presence of an effective amount (e.g. about 0.005% to 1% by weight of the alcohol weight) of a suitable alkaline catalyst(s) such as salts or hydroxides of the alkali metals or alkaline with metals. The preferred catalyst is KOH.

Poly(oxyalkylated) alcohols of the class RO—$(PO)_x$—$(EO)_y$—H may be made by methods similar to the above class except that the aliphatic alcohol or alcohols is first condensed with the PO, followed by capping with EO. Again, the moles of PO and EO employed will fall within the ranges of x and y as defined above.

Poly(oxyalkylated) alcohols of the class RO—$(PO)_x$—$(EO)_y$—$(PO)_z$—H may be made by methods similar to those described in U.S. Pat. No. 4,317,940, which issued to M. Scardera and F. Grosser on Mar. 2, 1982. The disclosure of this patent is incorporated herein by reference in its entirety. Generally, poly(oxyalkylated) alcohols of this class may be made by first condensing an aliphatic alcohol or alcohols of desired average chain length with PO, followed by reacting that condensation product with EO, followed by capping that intermediate product with more PO. The moles of PO, EO and PO per mole of alcohol employed in these reactions will fall within the ranges for x, y and z as given above. The preferred reaction temperature and catalysts would be the same as employed for the above-discussed classes of poly(oxyalkylated) alcohols.

Poly(oxyalkylated) alcohols of the class RO—$(EO)_x$—$(PO)_y$—$(EO)_z$—H may be made by methods similar to the proceeding class except that the aliphatic alcohol or alcohols is first condensed with EO, followed by a reaction with PO, and capping with EO. Again the moles of EO, PO, and EO will fall within the ranges of x, y and z as defined above.

It should be noted that not all free radical initiators may be used for this reaction. Only peroxy-type free radical initiator may be employed. Other types of initiators are not suitable for this reaction. Typical peroxy-type free radical initiators include hydrogen peroxide and organo peroxides and hydroperoxides such as dibenzoyl peroxide, acetyl peroxide, benzoyl hydroperoxide, t-butyl hydroperoxide, di-t-butyl peroxide, lauroyl peroxide, butyryl peroxide, diisopropylbenzene hydroperoxide, cumene hydroperoxide, paramenthane hydroperoxide, diacetyl peroxide, dialphacumyl peroxide, dipropyl peroxide, diisopropyl peroxide, isopropyl-t-butyl peroxide, butyl-t-butyl peroxide, dilauroyl peroxide, difuroyl peroxide, ditriphenylmethyl peroxide, bis(p-methoxy-benzoyl) peroxide, p-monomethoxy-benzoyl peroxide, rubrene peroxide, ascaridol, t-butyl peroxybenzoate, diethyl peroxyterephthalate, propyl hydroperoxide, isopropyl hydroperoxide, n-butyl hydroperoxide, t-butyl hydroperoxide, cyclohexyl hydroperoxide, trans-Decalin hydroperoxide, alpha-methylbenzyl hydroperoxide, alpha-methyl-alpha-ethyl benzyl hydroperoxide, Tetralin hydroperoxide, triphenylmethyl hydroperoxide, diphenyl-methyl hydroperoxide, 2,5-di-methyl-2,5-bis(2-ethyl hexanoyl peroxy)hexane, 1,1-bis(t-butyl-peroxy) cyclohexane and t-butyl perbenzoate.

As stated above, the weight ratio of the total poly(oxyalkylated) alcohol(s) employed to the unsaturated dicarboxylic acid should be from about 95:5 to about 40:60. When less than about 5 parts by weight of the acid is used per about 95 parts of the alcohol, the character of the alcohol is hardly changed and this reaction is meaningless for most applications. When more than about 60 parts by weight of the acid is employed per about 40 parts of the alcohol, there is a good chance that a significant portion of the acid will not react onto the alcohol because of absence of sufficient reactive sites. Preferably, this weight ratio is from about 90:10 to about 60:40.

Besides the selected reactants, peroxy-type initiators and weight ratios mentioned above, the other reaction conditions of this step are not critical to the present invention and the present process should not be limited to any particular conditions. It is preferred to carry out this reaction at a temperature from about 25° C. to about 150° C. More preferably, the reaction temperature may be in the range from about 80° C. to about 130° C. The reaction temperature should be high enough to activate the peroxy-type free radical initiator for this reaction. In some cases, it may be desirable to add a free radical accelerator such as a Redox catalyst to speed up the reaction. The reaction time will depend mainly upon the reaction temperature used and suitable reaction times will range from about 30 minutes to 600 minutes. The reaction may be monitored by following the disappearance of the maleic or fumaric acid in the reaction mixture with conventional analysis techniques.

Generally, this reaction may be carried out without a solvent. However, in some cases, it may be desirable to employ a solvent. For example, if a very viscous poly(oxyalkylated) alcohol is employed, it may be desirable to thin the reaction mixture with water or another solvent to facilitate the reaction.

Furthermore, super- or sub-atmospheric reaction pressure is not necessary for the present reaction. Atmospheric pressure is preferred in order to avoid the expense of special reaction vessels.

The free-radical initiated reaction of this invention may be conducted under conditions known to be suitable for free-radical polymerizations. The reaction is advantageously carried out by mixing the reactants, initiator(s), and optionally with a free-radical accelerator(s) and solvent, at temperatures from about 25° C. to about 150° C. with an inert atmosphere (e.g. under a nitrogen blanket) until the reaction is complete. The initiator(s) and optional catalyst(s) and solvent may be added at the beginning of the reaction or may be added portionwise at intervals during the course of reaction.

Likewise, the unsaturated acid reactant(s) and the poly-(oxyalkylated) alcohol(s) reactants may be brought together at the beginning of the reaction or may be combined in increments as the reaction proceeds.

The adducts produced by this reaction are generally water-insoluble, but they may be converted into water-dispersible form by reaction with a conventional neutralization agent (e.g. an inorganic or organic base) which converts some or all of the carboxylic acids groups into ionic groups according to well known methods.

2. Neutralization Of The Addition Product

As stated above, the formed addition product is neutralized in accordance with this invention in order to convert at least a major portion (i.e. at least 50%) of the carboxylic acid groups on the addition product.

Any conventional neutralizing agent may be employed. Preferred agents include water soluble tertiary amines (e.g. triethylamine), alkali metal hydroxides and mixtures thereof. The most preferred neutralization agents are sodium hydroxide and potassium hydroxide.

The amount of neutralization agent added is preferably sufficient to convert substantially all (i.e. above about 95%) of the carboxylic acid groups in the addition product to salt groups (e.g.—$COO^{\ominus}Na^{\oplus}$). The presence of these salt groups allows the composition to be caustic- and water-soluble. It should be noted that the neutralization agent may also be a caustic-containing processing bath or the like in which the surfactant is to be used. In this latter case, it may be desirable to merely add the unneutralized (or free-acid) adduct of the present invention and allow the neutralization to take place in-situ.

Basically, the surfactant compositions of the present invention consist of four components—an aliphatic alcohol, ethylene oxide, propylene oxide, and neutralized carboxylic acid groups. The alcohol serves as a hydrophobic, oil-soluble portion of the surfactant. The ethylene oxide is a hydrophilic water-soluble element of the surfactant. However, the ethylene oxide block is susceptable to degradation in caustic and other alkaline solutions. Such instability renders such surfactants incompatible in various compositions used in industrial household and institutional applications. To improve the alkali stability, the propylene oxide block is also present. This PO block also provides a low foaming tendency and hydrophobicity. The neutralized carboxylic acid groups provide the compositions with aqueous and caustic solubility. If biodegradable characteristics are desired, then it is preferred that the aliphatic alcohol be substantially linear with essentially no branching. This linearity is vital to the biodegradability of the surfactant product. Accordingly, the surfactant compositions of the present invention, therefore, may be biodegradable, both water and caustic soluble, have low to moderate foaming, while being stable with dry caustic.

3. Use Of Compositions As Surfactants

The advantageous properties of the surfactant compositions of the present invention may be useful in a variety of applications, in particular in dishwashing detergent formulations, as wetting, washing and dispersing agents in the textile, leather, paper, paint, pharmaceutical and cosmetic industries, as well as for household applications. Specifically, the anionic surfactants of the present invention may be used as surface active agents or emulsifiers in aqueous mixture (e.g. solutions, suspensions and the like) containing at least about 10%, more preferably from about 15% to about 35%, by weight of an alkali metal hydroxide (e.g. NaOH and KOH).

The following examples are provided to further illustrate the invention. All parts and percentages are by weight unless otherwise specified.

EXAMPLE 1

A 500-ml 3-necked round bottom flask containing a mechanical stirrer was fitted with a thermometer and nitrogen inlet. POLY-TERGENT® SL-62[1], 67.09 g (0.1 mole), and fumaric acid [23.2 g (0.2 mole)] was placed in the flask and the contents stirred and heated with a heating mantle placed under the flask. Upon attaining a temperature of 125° C., 3 mls of a free radical initiator, 1,1-bis (t-butyl peroxy) cyclohexane[2], were added over a 4-hour period in 1 ml increments. The reaction mixture was stirred at reaction temperature an additional 15-20 minutes. The product, the dibasic acid adduct of POLY-TERGENT® SL-62, weighed 93 g. One gram of the product was neutralized with sodium hydroxide (50% solution) and vacuum stripped to remove water. A 1% solution of this product—the POLY-TERGENT® SL-62/2 mole sodium fumarate adduct—was soluble in 10% sodium hydroxide solution.

[1] A $C_{6-10}$ linear aliphatic alcohol—3 mole oxypropyl—8 mole oxyethyl adduct, a product of Olin Corporation of Stamford, Conn.
[2] USP-400P (75% active), a product of Witco Chemical Corporation

EXAMPLE 2

Same procedure as Example 1, except that fumaric acid [34.8 g (0.3 mole)] was reacted and 5 mls of 1,1-bis (t-butyl peroxy) cyclohexane were employed as the free radical initiator. A 1% solution of the final product the POLY-TERGENT TM SL-62/3 mole sodium fumarate adduct, was soluble in 15% sodium hydroxide solution.

EXAMPLE 3

Same procedure as Example 1, except that fumaric acid [46.4 g (0.4 mole)] was reacted and 10 mls of 1,1-bis (t-butyl peroxy) cyclohexane were employed as the free radical initiator. A 1% solution of the final product—the POLY-TERGENT® SL-62/4 mole sodium fumarate adduct—was soluble in 30% sodium hydroxide solution.

EXAMPLE 4

Same procedure as Example 1, except that POLY-TERGENT® SLF-18[1] [177.9 g (0.1 mole)] and fumaric acid [46.4 g (0.4 mole)] were reacted. The free radical initiator was 3,6,6,9,9-pentamethyl 3(ethyl acetate) 1,2,4,5-tetraoxacyclononane[2](4 mls). A 1% solution of the final product—the POLY-TERGENT® SLF-18/4 mole sodium fumarate adduct—was soluble in 20% sodium hydroxide solution.

[1] A $C_{12-15}$ linear alcohol mixture—3 mole oxypropyl—12 mole oxyethyl—16 mole oxypropyl adduct, a product of Olin Corporation of Stamford, Conn.
[2] USP-138 (90% active), a product of Witco Chemical Corporation

EXAMPLE 5

Same procedure as Example 1, except that POLY-TERGENT® S-405 LF[1] [80.4 g (0.05 mole)] and fumaric acid [23.2 g (0.2 mole)] were reacted. The free radical initiator was ethyl-3,3-bis(t-butyl peroxy) butyrate[2] (4 mls). A 1% solution of the final product—the POLY-TERGENT® S-405 LF/4 mole sodium fumarate adduct—was soluble in 25% sodium hydroxide solution.

[1] A $C_{12-15}$ linear alcohol 12 mole oxyethyl— 15 oxypropyl adduct—a product of Olin Corporation of Stamford, Conn.
[2] USP-333P (75% active), a product of Witco Chemical Corporation of Richmond, Calif. (U.S. Peroxygen Div.).

PHYSICAL AND SURFACE PROPERTIES DETERMINATION

EXAMPLES 1, 2, 3, 4 and 5

To illustrate the favorable surfactant properties of the sodium fumarate products of Examples 1, 2, 3, 4 and 5, the following tests were conducted, with results listed in Table A.

"Cloud Point" is an indication of water solubility. A 1% aqueous solution of the surfactant is heated until a point is reached where the surfactant begins to separate out, causing the solution to become turbid or cloudy. This is the "Cloud Point".

"Surface Tension" is the force related to the intermolecular attraction at a liquid-air interface. This property indicates the tendency of a liquid to spread or wet solid surfaces. (Per ASTM D 1331-56).

"Interfacial Tension" is the force related to the intermolecular attraction of a liquid-liquid or liquid-solid interface. This property is indicative of effective emulsification; bubble, film and foam formation and behavior; cleaning of fabrics; ore flotation; adhesives; etc. (Per ASTM D 1331-56)

"Draves Wetting Time" denotes the time required to wet a 5 g cotton skein in an aqueous solution of surfactant. This property is important to textile processing utility. (Per AATCC Method 17-1952)

"Ross-Miles Foam Height" is a measure of the foam height generated initially and remaining after five minutes in a surfactant solution. This test indicates both foaming tendency (low-moderate-high) and foam stability. (Per ASTM Method D 1173-53)

As Table A illustrates, the surfactant product of the present invention features good water solubility, as well as favorable wetting and emulsification capability. The Ross-Miles test results show that the surfactant achieves moderate to high initial foaming and adequately maintains such foam height. Solubility with alkali also is demonstrated.

TABLE A

| | SURFACE PROPERTIES | | | | |
|---|---|---|---|---|---|
| | Example | | | | |
| | 1 | 2 | 3 | 4 | 5 |
| Surfactant | SL-62 2F | SL-62 3F | SL-62 4F | SLF-18 4F | S-405LF 4F |
| Cloud Point, 1%°C. | 100 | 100 | 100 | 100 | 76 |
| NaOH Solubility,* (%) | 10 | 15 | 30 | 20 | 30 |
| Surface Tension, dynes/cm | | | | | |
| 0.001 | 62 | 56 | 59 | 50 | 43 |
| 0.01 | 42 | 42 | 46 | 38 | 33 |
| 0.1 | 31 | 33 | 36 | 32 | 32 |
| Interfacial Tension, dynes/cm | | | | | |
| 0.001 | 25 | 27 | 31 | 18 | 13 |
| 0.01 | 16 | 17 | 21 | 8 | 7 |
| 0.1 | 9 | 9 | 12 | 3 | 6 |
| Draves | | | | | |

TABLE A-continued

| | SURFACE PROPERTIES | | | | |
|---|---|---|---|---|---|
| | Example | | | | |
| | 1 | 2 | 3 | 4 | 5 |
| Surfactant | SL-62 2F | SL-62 3F | SL-62 4F | SLF-18 4F | S-405LF 4F |
| Wetting Time, secs. | | | | | |
| @25° C. 0.10 | 134 | 180 | 180 | 105 | 70 |
| 0.25 | 30 | 40 | 76 | 29 | 32 |
| @60° C. 0.10 | 38 | 61 | 180 | 35 | 54 |
| 0.25 | 12 | 19 | 33 | 15 | 23 |
| Ross-Miles Foam Height, mm Initial/ after 5 mins. | | | | | |
| @25° C. 0.10 | 35/5 | 45/20 | 40/15 | 45/10 | 30/5 |
| 0.25 | 50/10 | 50/20 | 45/15 | 55/5 | 30/0 |
| @60° C. 0.10 | 60/15 | 80/15 | 65/20 | 50/5 | 50/5 |
| 0.25 | 80/10 | 105/10 | 100/10 | 75/10 | 55/5 |

*Solubility of 1% Surfactant in percentage of aqueous NaOH solution.

What is claimed is:

1. A surfactant composition made by the process comprising:
    a. forming a carboxylic acid group-containing additional product by reacting presence of a peroxy-type free-radical initiator an ethylenically unsaturated dicarboxylic acid selected from the group consisting of maleic acid, fumaric acid, and mixtures thereof, with at least one poly(oxyalkylated) alcohol having the formula:

$$R-O-(CH_2-CH-O)_x-(CH_2-CH-O)_y-(CH_2-CH-O)_zH$$
$$\quad\quad\quad\quad |\quad\quad\quad\quad\quad |\quad\quad\quad\quad\quad |$$
$$\quad\quad\quad\quad R_1\quad\quad\quad\quad\quad R_2\quad\quad\quad\quad\quad R_3$$

wherein R is a hydrocarbon-containing radical having an average of from about 6 to about 18 carbon atoms; $R_1$, $R_2$, and $R_3$ are individually selected from hydrogen and methyl with the proviso that $R_2$ is different than $R_1$ and $R_3$; x is an integer having a value from 1 to about 25; y is an integer having a value from about 1 to about 25; and z is an integer from about 0 to about 25; in the said weight ratio of said poly(oxyalkylated) alcohol to said dicarboxylic acid being from about 95:5 to about 40:60; and
    b. neutralizing said addition product with a sufficient amount of a neutralizing agent to convert at least a major portion of said carboxylic acid groups to salt groups.

2. The composition of claim 1 wherein R is a linear, aliphatic hydrocarbon radical having an average of from about 8 to about 14 carbon atoms.

3. The composition of claim 1 wherein x is an integer having a value from about 2 to about 12.

4. The compostition of claim 1 wherein y is an integer having a value from about 2 to about 15.

5. The composition of claim 1 wherein z is an integer having a value from about 0 to about 15.

6. The surfactant composition of claim 1 wherein the weight ratio of said poly(oxyalkylated) alcohol to said dicarboxylic acid is from about 90:10 to about 60:40.

7. The surfactant composition of claim 1 wherein said addition product is neutralized with a sufficient amount of a neutralization agent to convert at least substantially all of carboxylic acid groups to salt groups.

8. A surfactant composition made by the process comprising:
   a. forming a carboxylic acid group-containing additional product by reacting presence of a peroxy-type free-radical initiator an ethylenically unsaturated dicarboxylic acid selected from the group consisting of maleic acid, fumaric acid, and mixtures thereof, with at least one poly(oxyalkylated) alcohol having the formula:

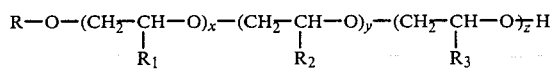

wherein R is a hydrocarbon-containing radical having an average of from about 6 to about 18 carbon atoms; $R_1$, $R_2$, and $R_3$ are individually selected from hydrogen and methyl with the proviso that $R_2$ is different than $R_1$ and $R_3$; x is an integer having a value from 1 to about 25; y is an integer having a value from 1 to about 25; and z is an integer from about 0 to about 25; in the said weight ratio of said poly(oxyalkylated) alcohol to said dicarboxylic acid being from about 95:5 to about 40:60.

9. An aqueous solution comprising water and at least about 10% by weight of an alkali metal hydroxide and an effective surface active amount of the surfactant of claim 1.

* * * * *